US007981256B2

(12) United States Patent
Wegerer et al.

(10) Patent No.: US 7,981,256 B2
(45) Date of Patent: Jul. 19, 2011

(54) SPLITTER WITH MULTI-STAGE HEAT PUMP COMPRESSOR AND INTER-REBOILER

(75) Inventors: David A. Wegerer, Des Plaines, IL (US); Paul A. Sechrist, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 809 days.

(21) Appl. No.: 11/937,796

(22) Filed: Nov. 9, 2007

(65) Prior Publication Data
US 2009/0120780 A1   May 14, 2009

(51) Int. Cl.
*B01D 1/28*   (2006.01)
*B01D 3/02*   (2006.01)
*C07C 7/04*   (2006.01)
*F25B 30/02*  (2006.01)

(52) U.S. Cl. ....... 203/26; 62/238.5; 62/238.7; 62/324.1; 62/498; 202/153; 202/182; 202/202; 203/27; 203/98; 203/99; 203/DIG. 4; 203/DIG. 8; 203/DIG. 19; 203/DIG. 25; 585/809

(58) Field of Classification Search ............... 62/238.5, 62/238.7, 324.1, 498; 159/24.1, 24.2, 47.1, 159/901; 202/153, 182, 202; 203/1, 3, 26, 203/27, 98, 99, DIG. 4, DIG. 8, DIG. 19, 203/DIG. 25; 585/809

See application file for complete search history.

(56) References Cited

U.S. PATENT DOCUMENTS

| | | | | |
|---|---|---|---|---|
| 2,509,136 A | * | 5/1950 | Cornell | 203/3 |
| 2,619,814 A | * | 12/1952 | Ludwig | 62/628 |
| 3,509,728 A | * | 5/1970 | Charlesworth et al. | 62/622 |
| 3,575,007 A | | 4/1971 | Gunther | |
| 4,056,444 A | * | 11/1977 | Weicht et al. | 203/26 |
| 4,177,111 A | * | 12/1979 | Pieper et al. | 203/14 |

(Continued)

FOREIGN PATENT DOCUMENTS
EP    0010253 A1    4/1980

OTHER PUBLICATIONS
Office Action dated Nov. 19, 2010 for U.S. Appl. No. 11/934,321, Sechrist.

(Continued)

*Primary Examiner* — Virginia Manoharan
(74) *Attorney, Agent, or Firm* — James C Paschall (57) ABSTRACT

A splitter system is disclosed that produces a product stream from a mixed stream of two materials with similar boiling points. A multi-stage heat pump compressor is used in combination with a bottoms reboiler and an intermediate reboiler resulting in reduced utility consumption. The appropriately placed intermediate reboiler enables use of a lower temperature heat source relative to the bottoms reboiler heat source. As a result, a lower pressure overhead vapor stream can be used to deliver heat to both the intermediate and bottoms reboilers, thereby conserving energy. The first stage of the multi-stage heat pump compressor delivers pressurized overhead vapor to the intermediate reboiler and the second stage provides pressurized overhead vapor to the bottoms reboiler. The disclosed design and method lessens the heat pump compressor power consumption and trim condenser duty for a propylene/propane splitter system by over 20%. A third stage of compression upstream of the overhead trim condenser may be used for purposes of making the column pressure and temperatures independent of the trim condenser temperature.

20 Claims, 3 Drawing Sheets

U.S. PATENT DOCUMENTS

| | | | |
|---|---|---|---|
| 4,234,391 A | | 11/1980 | Seader |
| 4,277,268 A | | 7/1981 | Spangler, Jr. |
| 4,336,046 A | * | 6/1982 | Schorre et al. ............. 62/623 |
| 4,539,076 A | | 9/1985 | Swain |
| 4,559,108 A | * | 12/1985 | Ahlberg .................. 202/154 |
| 4,615,769 A | | 10/1986 | Horigome et al. |
| 4,737,177 A | | 4/1988 | Erickson |
| 4,773,968 A | * | 9/1988 | O'Connell et al. ............ 203/26 |
| 4,961,826 A | | 10/1990 | Grethlein et al. |
| 5,000,841 A | | 3/1991 | Owen |
| 5,142,884 A | * | 9/1992 | Scaringe et al. ............ 62/324.4 |
| 5,351,492 A | | 10/1994 | Agrawal et al. |
| 5,360,533 A | | 11/1994 | Tagamolila et al. |
| 5,368,691 A | | 11/1994 | Asselineau et al. |
| 5,379,598 A | * | 1/1995 | Mostello .................. 62/646 |
| 5,435,436 A | | 7/1995 | Manley et al. |
| 5,584,985 A | | 12/1996 | Lomas |
| 5,737,940 A | | 4/1998 | Yao et al. |
| 5,858,206 A | | 1/1999 | Castillo |
| 6,045,660 A | | 4/2000 | Savage et al. |
| 6,113,776 A | | 9/2000 | Upson |
| 6,348,137 B1 | | 2/2002 | Nommensen |
| 6,538,169 B1 | | 3/2003 | Pittman |
| 6,558,515 B1 | | 5/2003 | Steacy |
| 6,605,190 B1 | | 8/2003 | Salamon et al. |
| 6,682,633 B1 | | 1/2004 | Xu et al. |
| 6,843,906 B1 | | 1/2005 | Eng |
| 7,138,534 B2 | | 11/2006 | Forlin et al. |
| 7,199,068 B2 | | 4/2007 | Winder et al. |
| 7,267,746 B1 | | 9/2007 | Harris et al. |
| 7,268,265 B1 | | 9/2007 | Stewart et al. |
| 7,687,674 B2 | | 3/2010 | Wegerer |
| 7,824,542 B2 | | 11/2010 | Menzel |
| 2006/0006054 A1 | | 1/2006 | Gobbel et al. |
| 2008/0161626 A1 | | 7/2008 | Wegerer |
| 2009/0114524 A1 | | 5/2009 | Sechrist |
| 2009/0308100 A1 | | 12/2009 | Jensen |
| 2010/0101273 A1 | * | 4/2010 | Sechrist et al. ............. 62/620 |
| 2010/0101930 A1 | * | 4/2010 | Sechrist et al. ............. 203/27 |
| 2010/0108487 A1 | | 5/2010 | Townsend |

OTHER PUBLICATIONS

Amendment dated Feb. 15, 2011 for U.S. Appl. No. 11/934,321, Sechrist.

Notice of Allowance dated Apr. 22, 2011 for U.S. Appl. No. 11/934,321, Sechrist.

\* cited by examiner

SPLITTER WITH MULTI-STAGE HEAT PUMP COMPRESSOR AND INTER-REBOILER

TECHNICAL FIELD

This disclosure relates generally to hydrocarbon processing. More specifically, this disclosure relates to the initial processing of hydrocarbon-containing materials into an intermediate stream including two materials with similar boiling points, e.g. propylene and propane, and the separation or splitting of those two materials.

BACKGROUND OF THE RELATED ART

Light olefins serve as feed materials for the production of numerous chemicals. Light olefins have traditionally been produced through the processes of steam or catalytic cracking of hydrocarbons such as derived from petroleum sources. Fluidized catalytic cracking (FCC) of heavy hydrocarbon streams is commonly carried out by contacting relatively high boiling hydrocarbons with a catalyst composed of finely divided or particulate solid material. The catalyst is transported in a fluid-like manner by transmitting a gas or vapor through the catalyst at sufficient velocity to produce a desired regime of fluid transport. Contact of the heavy hydrocarbons with the fluidized catalyst results in the cracking reaction.

FCC processing is more fully described in U.S. Pat. Nos. 5,360,533, 5,584,985, 5,858,206 and 6,843,906. Specific details of the various contact zones, regeneration zones, and stripping zones along with arrangements for conveying the catalyst between the various zones are well known to those skilled in the art.

The FCC reactor serves to crack gas oil or heavier feeds into a broad range of products. Cracked vapors from an FCC unit enter a separation zone, typically in the form of a main column, that provides a gas stream, a gasoline cut, light cycle oil (LCO), heavy cycle oil (HCO), and clarified oil (CO) components. The gas stream may include hydrogen and $C_1$ and $C_2$ hydrocarbons, and liquefied petroleum gas ("LPG"), i.e., $C_3$ and $C_4$ hydrocarbons.

There is an increasing need for light olefins such as propylene for the production of polypropylene, propyl benzene, cumene and the like. Research efforts have led to the development of an FCC process that produces or results in greater relative yields of light olefins, such as propylene. Such processing is more fully described in U.S. Pat. No. 6,538,169.

A conventional FCC process produces a combined propylene/propane stream. The recovery and purification of propylene from the combined propylene/propane is accomplished via a sequence of distillation operations. The sequence consists of distillation columns to separate both lower and higher boiling components from propylene and generally includes a distillation operation to separate a mixed stream of propane and propylene into a propylene product or "polymer grade" propylene, which can be used for polymer manufacturing in a downstream operation. The propane/propylene separation by distillation is both energy and capital intensive due to the relative volatility of species to be separated, feed composition, and product purity requirements of "polymer grade" propylene.

Because of the energy consumption requirements of splitter columns in general, splitter column configurations for similar boiling point materials that reduce utility consumption are desirable given increasing energy costs and a general need to reduce $CO_2$ emissions associated with fossil fuel consumption.

SUMMARY OF THE INVENTION

A splitter system is disclosed for separating a first material from a mixture of first and second materials. The system includes a column with a feed inlet that introduces a mixture of first and second materials to the column. Two reboiler-heat exchangers and two associated circulation loops are utilized. An intermediate loop is connected to the column below the feed inlet. The intermediate loop passes through an intermediate reboiler heat exchanger. As an alternative to the intermediate loop, the intermediate reboiler is a stab-in heat exchanger disposed within the column below the feed. A bottoms loop is connected to the bottom of the column with the bottoms loop passing through a bottoms reboiler heat exchanger. As an alternative to the bottoms loop, a stab-in heat exchanger may be utilized within the bottom of the column.

The top of the column comprises an overhead outlet connected to a first overhead loop and a second overhead loop. The first overhead loop connects the overhead outlet to a first heat pump compressor and the second overhead loop. The second overhead loop connects the first overhead loop to a second heat pump compressor.

The first heat pump compressor passes vapor from the first overhead loop through the intermediate reboiler heat exchanger at an elevated pressure to heat and at least partially vaporize the intermediate material exposed to the intermediate reboiler. The second heat pump compressor passes material from the second overhead loop at an elevated pressure through the bottoms reboiler heat exchanger to heat and at least partially vaporize the bottoms material exposed to the bottoms reboiler. The first and second heat pump compressors act to increase the pressure of the first and second overhead loop vapor streams, thereby increasing their respective condensation temperatures to enable the first and second overhead loop streams to deliver heat to the intermediate and bottoms reboilers.

The use of two heat pumps, two overhead vapor loops and the additional intermediate reboiler results in substantial energy savings as shown below. The energy savings opens the possibility of using stab-in heat exchanger for the inter-reboiler and bottoms reboiler, depending upon the separation being carried out.

In a refinement, the first heat pump compressor and the second heat pump compressor are first and second stages of a two stage heat pump compressor.

In another refinement, when the column is operated at a lower pressure, a small flow third stage of compression can be employed between the second stage of compression and the trim condenser, to decouple the operating temperatures of the column from the trim condenser temperature. In such a refinement, a third overhead loop is provided which connects the second overhead loop with a third heat pump compressor disposed upstream of a trim condenser. In such a design, a three stage heat pump compressor may be employed.

In another refinement, receiving drums are disposed upstream of each heat pump compressor or each heat pump stage. More specifically, the first overhead loop passes through the first heat pump compressor and through a second receiving drum that has a vapor outlet connected to second heat pump compressor and a liquid outlet connected to a first receiving drum. The first receiving drum has a vapor outlet connected to the first heat pump compressor and a liquid outlet connected to a reflux pump that is connected to the reflux inlet as well as a first product outlet. The second overhead loop passes through the second heat pump compressor to a trim condenser before passing through to the second receiving drum. Liquid from the second receiving drum is passed to the first receiving drum.

The disclosed splitter systems preferably operate at a reflux to feed ratio (R/F) of about 5 or greater. Because of the employment of multi-stage heat pump compressors in preferred embodiments, the disclosed splitter systems are particularly beneficial for separating materials having a difference in boiling points of about 11° C. (20° F.) or less.

In one embodiment, the first material is propylene and the second material is propane. For a propylene/propane splitter, the column houses from about 120 to about 220 theoretical stages, more preferably from about 150 to about 190, still more preferably about 170. Further, the feed inlet may be connected to the column above about the $120^{th}$ stage counting from the top of the column. Also, the intermediate loop outlet may be connected to the column above about the $149^{th}$ stage counting from the top of the column. The number of stages will vary greatly, depending upon the two materials being separated and the ratio of the two materials in the feed.

For a propylene/propane splitter, the first heat pump compressor pressurizes vapor taken from the first overhead loop to a pressure exceeding 1379 kPaa (200 psia) and the second heat pump compressor pressurizes vapor from the second overhead loop to a pressure exceeding 1725 kPaa (250 psia).

However, this disclosure is not limited to a propylene/propane splitter or even to a light olefin/paraffin splitter. The apparatuses and techniques disclosed herein are applicable to any two materials with similar boiling points, examples of which are too numerous to list here.

A method for separating a first material from a mixture of the first material and a second material is also disclosed. The disclosed includes introducing the mixture into a column through a feed inlet disposed between a top and a bottom of the column. The method further comprises delivering heat to intermediate and bottoms reboilers via overhead vapor taken from the top of the column and circulated at elevated pressures through first and second overhead loops that pass through the intermediate and bottoms reboilers.

Other advantages will be apparent to those skilled in the art from the following detailed description taken in conjunction with the appended claims and drawings.

DETAILED DESCRIPTION

Figure 1:
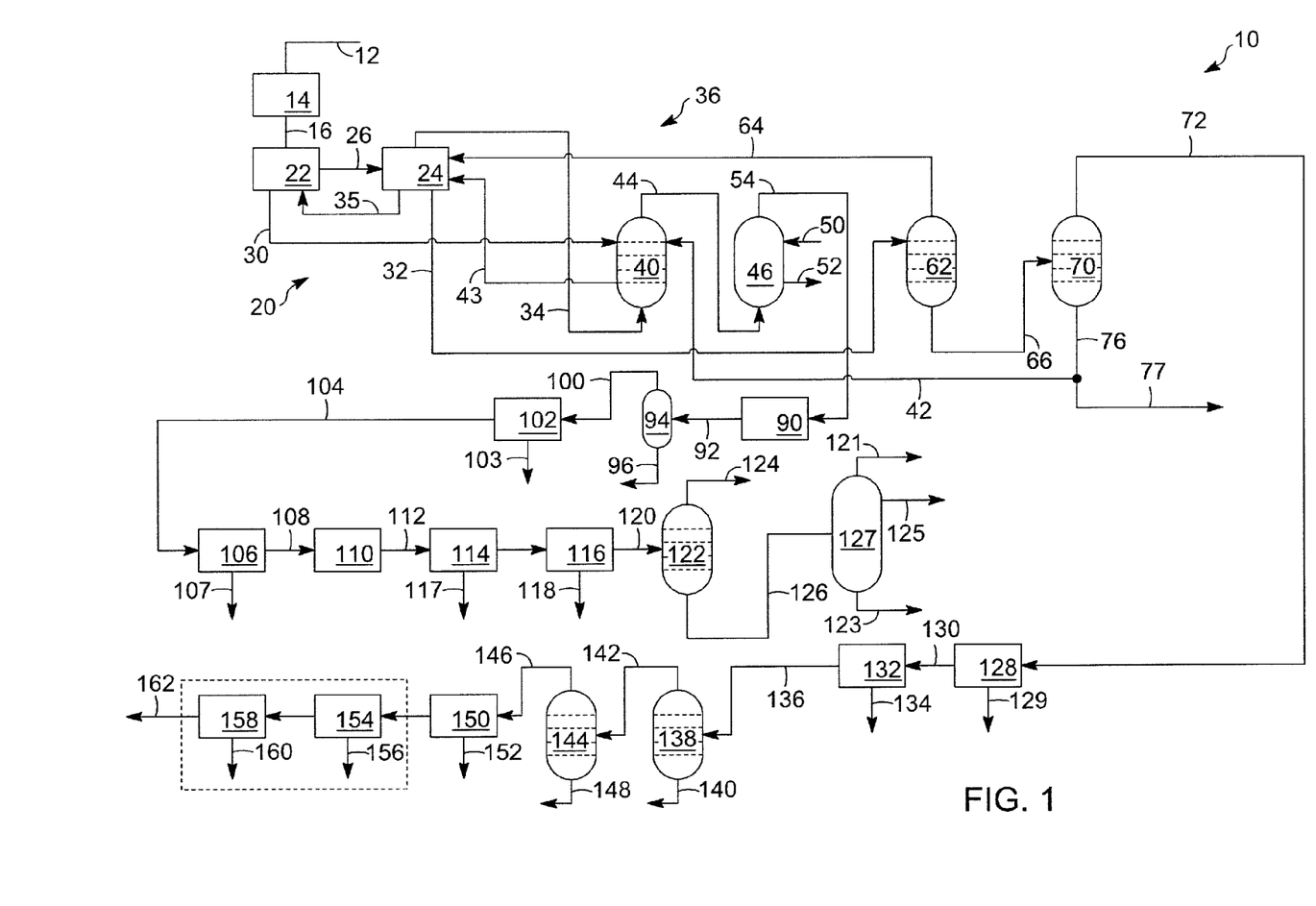
FIG. 1 is a simplified schematic diagram of a system for catalytic cracking a heavy hydrocarbon feedstock and obtaining selected hydrocarbon fractions, including light olefins, via an absorption-based product recovery.
Figure 2:
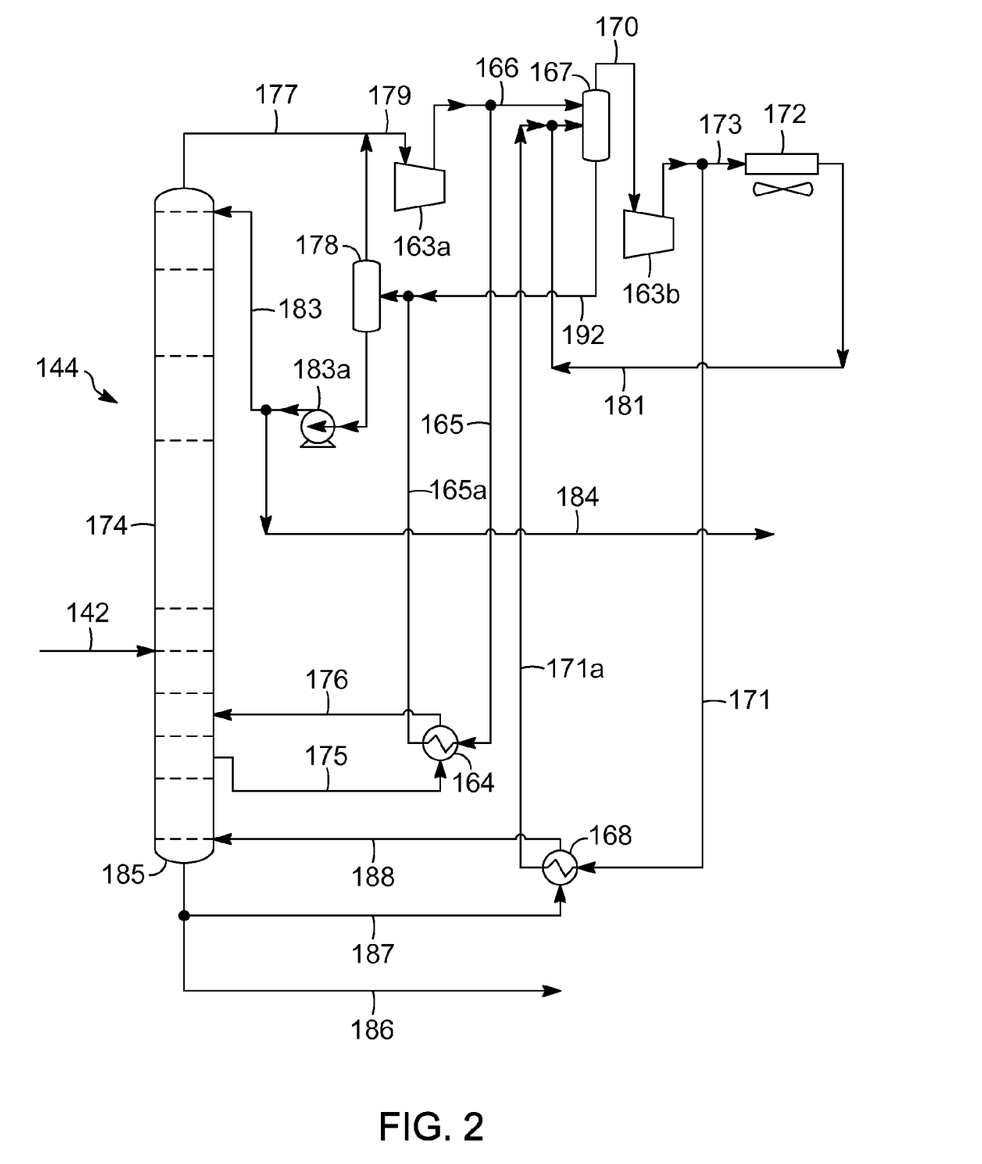
FIG. 2 is a simplified schematic diagram of an energy efficient splitter column configuration for the splitter 144 shown in FIG. 1 for separating a two similar boiling point materials, in accordance with this disclosure.
Figure 3:
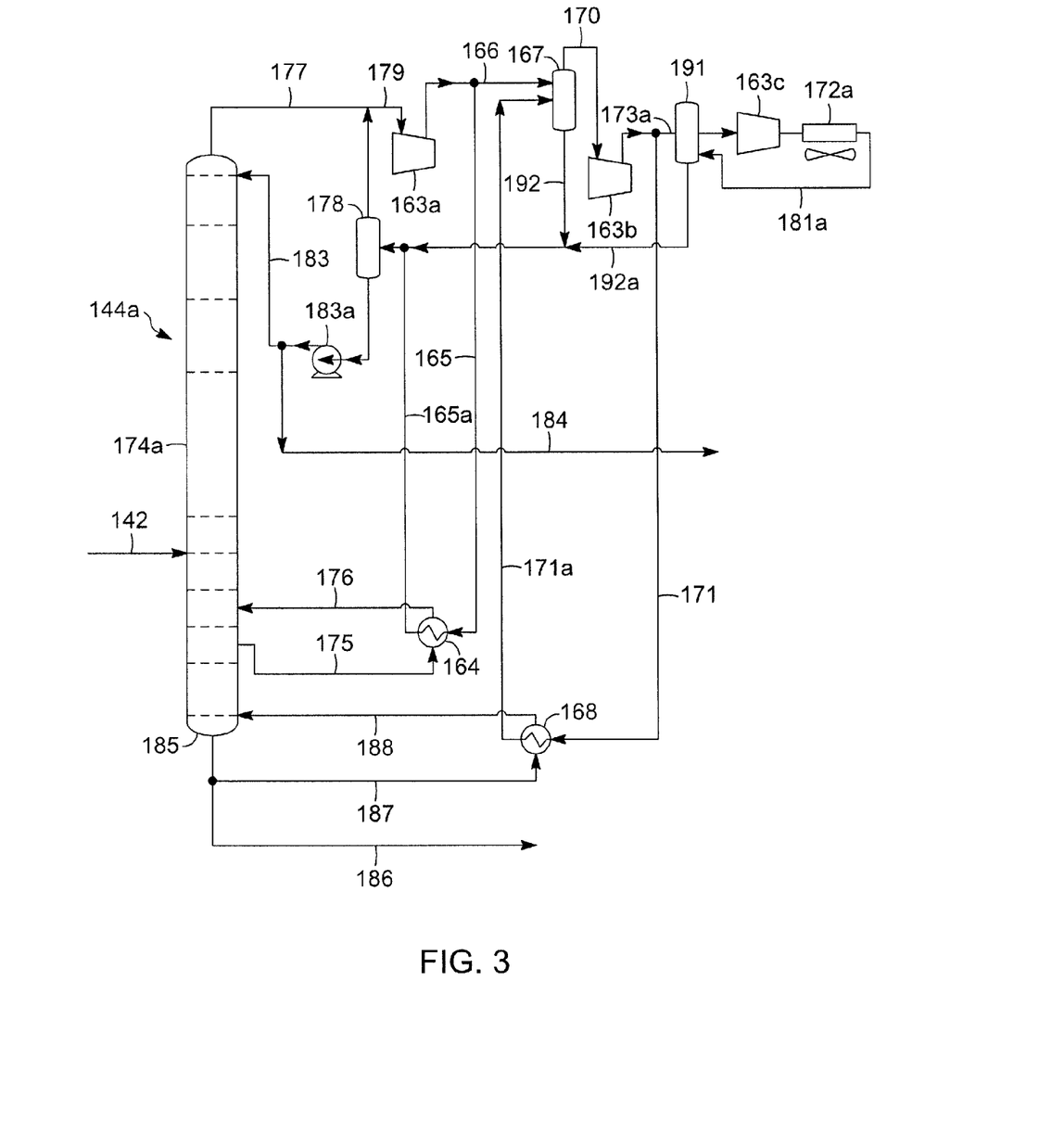
FIG. 3 is another simplified schematic diagram of an energy efficient splitter column configuration for the splitter 144 shown in FIG. 1 for separating two similar boiling point materials, in accordance with this disclosure.

FIG. 1 schematically illustrates a system 10 for catalytic cracking a heavy hydrocarbon feedstock and obtaining light olefins via absorption-based product recovery and FIGS. 2 and 3 schematically illustrate splitter columns 144, 144a and system for separating two similar boiling point materials, e.g., a light olefin, such as propylene, from a mixture of the olefin and paraffin, such as a propylene/propane mixture. However, it will be noted again that the splitter systems of FIGS. 2 and 3 are not limited to a light olefin/paraffin or a propylene/propane separation.

The systems disclosed in FIGS. 2 and 3 are applicable to the separating of any two like-boiling point materials and are particularly useful for materials with a difference in boiling points of about 11° C. (~20° F.) or less. Non-limiting examples of separations suitable for the systems 144, 144a of FIGS. 2 and 3 include: paraffin/olefin separations including ethane/ethylene, propane/propylene, butane/butylene, pentane/pentene; isomer/normal separations of these compounds (e.g., isobutane/butane); straight chain/branched or multi-chain paraffin separations; ethyl benzene/styrene; mixed xylenes separations (e.g., para/ortho/meta); and others.

Those skilled in the art and guided by the teachings herein provided will recognize and appreciate that the illustrated systems 10, 144, 144a have been simplified by the elimination of various usual or customary pieces of process equipment including some heat exchangers, process control systems, pumps, fractionation systems, and the like. It may also be discerned that the process flows depicted in FIGS. 1-3 may be modified in many aspects without departing from the scope of this disclosure.

In the cracking system 10, a suitable heavy hydrocarbon feedstock stream is introduced via a line 12 into a fluidized reactor zone 14 wherein the heavy hydrocarbon feedstock contacts a hydrocarbon cracking catalyst zone to produce a hydrocarbon effluent comprising a range of hydrocarbon products, including light olefins.

Suitable fluidized catalytic cracking reactor zones for use in the practice of such an embodiment may, as is described in above-identified U.S. Pat. No. 6,538,169, include a separator vessel, a regenerator, a blending vessel, and a vertical riser that provides a pneumatic conveyance zone in which conversion takes place. The arrangement circulates catalyst and contacts the catalyst with the feed. The various catalysts for FCC processes are known to those skilled in the art.

The relatively heavier feeds suitable for processing in accordance herewith include conventional FCC feedstocks or higher boiling or residual feeds. A common conventional feedstock is vacuum gas oil which is typically a hydrocarbon material prepared by vacuum fractionation of atmospheric residue and which has a broad boiling range of from 315-622° C. (600-1150° F.) and, more typically, which has a narrower boiling point range of from 343-551° C. (650-1025° F.). Heavy or residual feeds, i.e., hydrocarbon fractions boiling above 499° C. (930° F.), are also suitable. The fluidized catalytic cracking processing the invention is typically best suited for feedstocks that are heavier than naptha range hydrocarbons boiling above about 177° C. (350° F.).

The effluent or at least a selected portion thereof is passed from the fluidized reactor zone 14 through a line 16 into a hydrocarbon separation system 20, which includes a main column section 22 and a staged compression section 24. The main column section 22 may desirably include a main column separator with an associated main column overhead receiver wherein the fluidized reactor zone effluent can be separated into desired fractions including a main column vapor stream, which passes through the line 26, and a main column liquid stream, which passes through the line 30. Other fraction lines including a heavy gasoline stream, a light cycle oil ("LCO") stream, a heavy cycle oil ("HCO") stream and a clarified oil ("CO") stream, for example, are not specifically shown or described.

The main column vapor stream line 26 is introduced into the staged compression section 24, which may be a two-stage compression. The staged compression section 24 results in the formation of a high pressure separator liquid stream in a line 32 and a high pressure separator vapor stream in a line 34. While the pressure of the high pressure liquid and high pressure vapor may vary, in practice, such streams are typically at a pressure in the range of from about 1375 kPag to about 2100 kPag (about 200 psig to about 300 psig). The compression section 24 may also result in the formation of a stream of spill back materials largely composed of heavier hydrocarbon materials and such as can be returned to the main column section 22 via a line 35.

The high pressure separator liquid stream 32 may include $C_3+$ hydrocarbons and is substantially free of carbon dioxide and hydrogen sulfide. The high pressure separator vapor stream 34 may include $C_2-$ hydrocarbons and typically includes a quantity of carbon dioxide and hydrogen sulfide.

The separator vapor stream line 34 is introduced into an absorption zone 36, which includes a primary absorber 40. In the absorber 40, the separator vapor stream 34 makes contacts with a debutanized gasoline material provided by the line 42 and the main column overhead liquid stream 30 to absorb $C_3+$ materials and separate $C_2$ and lower boiling fractions from the separator vapor stream. In general, the absorption zone 36 includes the primary absorber 40 that may include a plurality of stages with at least one and preferably two or more intercoolers interspaced therebetween to assist in achieving desired absorption. In practice, the primary absorber 40 includes about five absorber stages between each pair of intercoolers. The primary absorber 40 may include from about 15 to about 25 ideal stages and from 2 to 4 intercoolers appropriately spaced therebetween.

$C_3+$ hydrocarbons absorbed in or by the debutanized gasoline stream 42 and main column liquid stream 30 can be passed via the line 43 back to the two-stage compressor 24 for further processing. The off gas from the primary absorber 40 passes via a line 44 to a secondary or sponge absorber 46. The secondary absorber 46 contacts the off gas with light cycle oil from a line 50. Light cycle oil absorbs most of the remaining $C_4$ and higher hydrocarbons and returns to the main fractionators via a line 52. A stream of $C_2-$ hydrocarbons is withdrawn as off gas from the secondary or sponge absorber 46 in the line 54 for further treatment as later described herein.

The high pressure liquid stream 32 from the compressor 24 proceeds to the stripper 62 which removes most of the $C_2$ and lighter gases through the overhead line 64 which passes to the compressor 24. In practice, the stripper 62 can be operated at a pressure ranging from about 1375 kPag to about 2100 kPag (about 200 psig to about 300 psig) with a $C_2/C_3$ molar ratio in the stripper bottoms of less than 0.001 and preferably with a $C_2/C_3$ molar ratio in the stripper bottoms of less than about 0.0002 to about 0.0004.

As shown in FIG. 1, the $C_2$ and lighter gases in the line 64 are combined in the compressor 24 with main column vapors from the line 26 to form with high pressure separator vapor stream 34 that is fed into the primary absorber 40. The stripper 62 supplies a liquid $C_3+$ stream 66 to the debutanizer 70. A suitable debutanizer 70 includes a condenser (not shown) that desirably operates at a pressure ranging from about 965 kPag to about 1105 kPag (from about 140 psig to about 160 psig), with no more than about 5 mol % $C_5$ hydrocarbons in the overhead and no more than about 5 mol % $C_4$ hydrocarbons in the bottoms. More preferably, the relative amount of $C_5$ hydrocarbons in the overhead ranges from less than from about 1 to about 3 mol % and the relative amount of $C_4$ hydrocarbons in the bottoms ranges from less than from about 1 to about 3 mol %.

A stream of $C_3$ and $C_4$ hydrocarbons from the debutanizer 70 are taken overhead by a line 72 for further treatment, as described below. The bottoms stream 76 from the debutanizer 70 comprises gasoline, part of which forms the stream 42 which is fed to the top of the primary absorber 40 where it serves as the primary first absorption solvent. Another portion of the stream of debutanized gasoline is passed through the line 77 to a naphtha splitter (not shown), which may be a dividing wall separation column.

$C_2-$ hydrocarbon stream 54 withdrawn from the secondary or sponge absorber 46 are passed through a further compression section 90 to form a compressed vapor stream 92 that is passed into a compression or discharge vessel 94. The discharge vessel 94 forms a liquid knockout stream generally composed of heavy components (e.g., $C_3+$ hydrocarbons that liquefy in the discharge vessel 94) and are withdrawn in the line 96. The discharge vessel 94 also forms an overhead vapor stream 100 that primarily comprising $C_2-$ hydrocarbons, with typically no more than trace amounts (e.g., less than 1 wt %) of $C_3+$ hydrocarbons.

The overhead stream 100 is connected to an amine treatment section 102 to remove $CO_2$ and $H_2S$. The utilization of amine treatment system 102 for carbon dioxide and/or hydrogen sulfide removal is well known in the art. Conventional amine treatment systems typically employ an amine solvent such as methyl diethanol amine [MDEA] to absorb or otherwise separate $CO_2$ and $H_2S$ from hydrocarbon stream materials. A stripper or regenerator is typically subsequently used to strip the absorbed $CO_2$ and $H_2S$ from the amine solvent, permitting the reuse of the amine solvent.

While such amine treatment has proven generally effective for removal of carbon dioxide from various hydrocarbon-containing streams, the use of amine treatment with ethylene-rich hydrocarbon and carbon dioxide-containing streams may result in some undesired complications as some of the olefin material may be co-absorbed with the $CO_2$ and $H_2S$ in or by the amine solvent. Such co-absorption of olefin material undesirably reduces the amounts of light olefins available for recovery from such processing. Moreover, during such subsequent stripper processing of the amine solvent, the presence of such olefin materials can lead to polymerization. Such polymerization can lead to degradation of the amine solvent and require expensive off-site reclamation processing.

In view the above, it may be desirable to utilize an amine treatment system that includes or incorporates a pre-stripper interposed between the amine system absorber and the amine system stripper/regenerator. Such an interposed pre-stripper, can desirably serve to separate hydrocarbon materials, including light olefins such as ethylene, from the carbon dioxide and amine solvent prior to subsequent processing through the regenerator/stripper. A $CO_2/H_2S$ outlet line is shown at 103.

The stream 104 containing $C_2-$ hydrocarbons substantially free of carbon dioxide proceeds to a dryer section 106 with a water outlet line 107. A stream containing dried $C_2-$ hydrocarbons substantially free of carbon dioxide and hydrogen sulfide passes via line 108 to an acetylene conversion section or unit 110. As is known in the art, acetylene conversion sections or units are effective to convert acetylene to form ethylene. Thus, an additionally ethylene-enriched process stream 112 is withdrawn from the acetylene conversion section or unit 110 and passed to the optional dryer 114 or to the $CO_2$, carbonyl sulfide ("COS"), arsine and/or phosphine treater 116 as is known in the art to effect removal of $CO_2$, COS, arsine and/or phosphine.

Water is withdrawn from the dryer 114 through the line 117. $CO_2$, COS, arsine and/or phosphine are withdrawn through the line 118, and the treated stream 120 is introduced into a demethanizer 122. A suitable demethanizer 122 may include a condenser (not specifically shown) that desirably operates at a temperature of no greater than about −90° C. (−130° F.), more preferably operates at a temperature in the range of from about −90° C. to about −102° C., preferably from about −96° C. (−130° to about −150° F., preferably at about −140° F.). In addition, the demethanizer 122 may operate with a methane to ethylene molar ratio in the bottoms of no greater than about 0.0005 and, more preferably at a methane to ethylene molar ratio in the bottoms of no greater than from about 0.0003 to about 0.0002.

The overhead stream 124 of methane and hydrogen gas from the demethanizer 122 may be used as a fuel or, if desired, taken for further processing or treatment such as to a pressure swing absorption unit (not shown) for $H_2$ recovery. The demethanizer outlet stream 126 passes to an ethane/ethylene ($C_2$—$C_2$=) splitter 127, which provides an ethylene product stream 125, an ethane stream 123 and off gas line 121.

The stream 72 containing $C_3$ and $C_4$ hydrocarbons taken overhead from the debutanizer 70 may contain some significant relative amounts of hydrogen sulfide and is therefore preferably passed to a hydrogen sulfide removal treatment unit 128, such as an amine treatment section, where hydrogen sulfide is removed through the line 129 and the treated stream 130 is passed to an optional extraction unit 132 to catalytically oxidize mercaptans present to disulfides via a caustic wash, which are removed through the line 134.

The resulting stream 136 is passed to the $C_3/C_4$ splitter 138. A suitable $C_3/C_4$ splitter includes a condenser (not specifically shown) that desirably operates at a pressure in the range of from about 1650 kPag to about 1800 kPag (from about 240 psig to about 260 psig), preferably at a pressure of about 1724 kPag (about 250 psig) and desirably operates such that there is no more than about 5 mol % $C_4$s in the overhead product stream, preferably less than about 1 mol % $C_4$s in the overhead product stream and no more than about 5 mol % $C_3$s in the bottoms stream, preferably less than about 1 mol % $C_3$s in the bottoms stream.

The $C_3/C_4$ splitter 138 forms a bottoms stream 140 of $C_4$+ hydrocarbons for use as either for product recovery or further desired processing. The $C_3/C_4$ splitter 138 also forms a stream 142 composed primarily of $C_3$ hydrocarbons which is passed to a propylene/propane splitter 144, shown in greater detail in FIG. 2. A suitable such propane/propylene splitter 144 may operate such that at least 98 wt % and, preferably, at least about 99 wt % of the propylene is recovered is in the overhead stream and the propylene in the overhead stream is at least about 99.5% pure.

Still referring to FIG. 1, the propylene/propane splitter 144 forms a propylene stream 146 and a propane 148 stream. The propylene stream 146 may be passed to dryer 150 for the removal of water through the line 152 before being passed on to a regenerative COS treater 154 to remove COS through the line 156 before being passed through the arsine and/or phosphine treater 158 to effect removal of trace amounts of arsine and/or phosphine through the line 160 and producing an propylene product stream 162.

Turning to FIG. 2, the propylene/propane (P/P) splitter 144 and associated equipment is shown in greater detail with a two stage heat pump compressor 163a, 163b and intermediate reboiler or inter-reboiler 164. The first stage of compression provided by the stage 163a delivers pressurized overhead vapor to both the inter-reboiler 164 through the line 165 and to the second compression stage 163b through the line 166, second stage suction drum 167 and line 170 as shown in FIG. 2. Increasing the pressure of the overhead vapor passing through the line 165 increases the condensation temperature of the overhead vapor thereby enabling the overhead material in the first overhead loop or circuit 179-163a-165-165a to deliver heat to the intermediate reboiler 164. The second compression stage 163b delivers pressurized overhead vapor to the bottom reboiler 168 via the line 171 and to the trim condenser 172 via the line 173. Increasing the pressure of the overhead vapor passing through the line 171 increases the condensation temperature of the overhead vapor thereby enabling the overhead material in the second overhead loop or circuit 166-167-170-163b-171-171a to deliver heat to the bottoms reboiler 168. Material is also circulated back to the second stage suction drum or vessel 167 through the line 181.

The splitter column 174 will need to accommodate about 170 theoretical distillation stages for the separation of propylene from propane, although the number of theoretical stages (NTS) may vary depending upon process conditions. The NTS for a P-P splitter column can range from about 150 to about 190. The feed 142 is introduced above about stage 120 (counting from the top). The inter-reboiler supply 175 is drawn from above about theoretical tray 149 (counting from the top) and the mixed vapor-liquid stream 176 from the inter-reboiler heat exchanger 164 is returned between about tray 148 and about tray 149. For this example, nearly 60% of the required distillation heat input is delivered via the inter-reboiler heat exchanger 164. The remaining heat input is supplied using the bottom reboiler 168. It will be noted that the inter-reboiler 164 may be a stab-in heat exchanger disposed within the column 174 thereby eliminated the need for the intermediate circulation loop shown at 175, 176.

The splitter overhead vapor stream 177 mixes with vapor from the first stage heat pump compressor suction drum 178. The combined vapor stream 179 flows to a first stage 163a of compression. In the example shown, the vapor stream 179 is pressurized from about 1218 kPaa (176.7 psia) to about 1687 kPaa (244.7 psia). At these pressures, the condensation temperature of the vapor is sufficient to enable heat input to the inter-reboiler heat exchanger 164.

Pressurized vapor from the first stage heat pump compressor 163a is delivered to the inter-reboiler heat exchanger 164 via the line 165 and to the second stage heat pump compressor suction drum 167 via the line 166. The second stage compressor 163b further pressurizes vapor received from the second stage compressor suction drum 167 via the line 170. In this example, the vapor in the drum 167 is pressurized by the second stage compressor 163b from about 1618 kPaa (234.7 psia) to about 2046 kPaa (296.7 psia). At these pressures, the condensation temperature of the vapor is sufficient to enable heat input to the bottom reboiler 168 and to reject heat in excess of that required for distillation through the trim condenser 172 using an ambient cooling utility.

The liquid condensate from the bottoms reboiler heat exchanger 168 and the effluent from the trim condenser 172 are returned to the second stage compressor suction drum 167 via the lines 171a and 181, respectively. The liquid condensate from the intermediate reboiler heat exchanger 164 and the liquid from the second stage compressor suction drum 167 are delivered to the first stage compressor suction drum 178. The liquid from the first stage compressor suction drum 178 may include net propylene product and distillation column reflux. The reflux may be returned to the splitter column 174 through the line 183 or elsewhere and the net propylene may be drawn off as purified product through the line 184. Preferably, a molar ratio of material returning to the column 174 through the line 183 to material entering the column 174 through the feed inlet 142 (R/F) is about five or more. Another material may be used as the reflux material. Net propane product is withdrawn from the splitter column bottom stage 185 through the outlet line 186. A bottoms recycle line 187 passes through the bottom reboiler 168 and returns to the P/P splitter column 174 through the line 188. Instead of the bottoms material loop 187, 188, the bottoms reboiler 168 may be a stab-in heat exchanger disposed within the vessel 174.

The disclosed splitter system 144a includes a combination of unique circulation loops or circuits that conserve substantial amounts of energy. A first overhead vapor circulation loop includes the overhead vapor passing to the first stage heat pump compressor 163a where the overhead vapor is pressurized before it is passed through the intermediate reboiler heat exchanger 164 via the lines 165, 165a. The cooled vapor/condensate material (which has just transmitted heat to the material flowing through the intermediate loop 175, 176) passes into the first stage compressor suction drum 178. A portion of the condensed material in the drum 178 may be pumped back into the column 174 by the reflux pump 183a via the line 183. Another portion of the material may be taken through the line 184 as propylene product. Thus, the pressurized overhead vapor of the first overhead vapor loop delivers heat to the intermediate reboiler or inter-reboiler heat exchanger 164.

A second overhead loop is represented by the second stage suction drum 167, line 170 and the second stage heat pump compressor 163b. Compressed overhead material from the second stage compressor 163b is circulated through the bottoms reboiler heat exchanger 168 before it is returned to the suction drum 167. Condensate from this suction drum 167 is then passed to the suction drum 178 through the line 192. Thus, the second overhead vapor loop delivers heat to the bottoms reboiler 168 and two separate overhead vapor loops are used to deliver heat to the intermediate reboiler heat exchanger 164 and bottoms reboiler heat exchanger 168.

In a conventional splitter system with a single bottom reboiler, in order to achieve an appropriate separation for polymer grade propylene, the bottoms liquid enters the bottoms reboiler at about 40.6° C. (105° F.) and returns to the column at about 41.1° C. (106° F.). This requires the heat pump compressor vapor delivering heat to the bottoms reboiler to enter the single bottoms reboiler at a temperature of about 57.2° C. (135° F.) and to exit the reboiler at a temperature of about 48.9° C. (120° F.).

Similarly, the bottoms reboiler 168 of this disclosure may be supplied with pressurized vapor from the heat pump compressor 163b at a temperature of about 57.2° C. (135° F.) with condensate returned to the suction drum 167 at a temperature of about 48.9° C. (120° F.) for purposes of heating the bottoms liquid from about 40.6° C. (105° F.) to about 41.1° C. (106° F.). However, the first heat pump compressor 163a can supply the inter-reboiler 164 with pressurized vapor at about 45.6° C. (114° F.) and returning condensate to the suction drum 178 at a temperature of about 40° C. (104° F.). This results in the material flowing through the intermediate loop 175, 176 being heated from a temperature of about 33.3° C. (92° F.) to about 33.4° C. (92.2° F.), which, as shown in Tables 1 and 2 below, provides an energy savings of at least 20%.

Table 1 summarizes a utility consumption for a conventional P-P Splitter incorporating a typical (single stage) heat pump compressor design with no inter-reboiler and the two stage heat pump compressor 163a, 163b with inter-reboiler 164 configuration shown in FIG. 2. The example shows the disclosed dual stage splitter system 144 of FIG. 2 lessens the heat pump compressor power consumption and trim condenser duty by over 20%.

TABLE 1

P-P SPLITTER FEED AND PRODUCT DATA

| | Feed/Product |
|---|---|
| Feed Rate (MT/day) | 4,584 |
| Feed Propylene (wt %) | 86.0 |
| Propylene Product (MT/day) | 3,923 |
| Propylene Purity (wt %) | 99.5 |

TABLE 2

COMPARISON OF CONVENTIONAL P-P SPLITTER WITH P-P SPLITTER OF FIG. 2

| | Conventional Single Stage Heat Pump Compressor Configuration | Two-Stage Heat Pump Compressor With Inter-Reboiler |
|---|---|---|
| Total Theoretical Trays | 170 | 170 |
| Feed Tray From Top | 120 | 120 |
| Inter-Reboiler Tray From | n/a | 149 |
| Trim Condenser Duty, (MMBtu/hr) | 78 | 60 |
| Bottom Reboiler Duty, (MMBtu/hr) | 675 | 277 |
| Inter-Reboiler Duty, (MMBtu/hr) | n/a | 400 |
| Heat Pump, HP ($1^{st}$ Stage/$2^{nd}$ Stage) | 29,100 29,100/0 | 22,500 16,600/5,900 |

Preferably, but not necessarily, the heat pump compressor stages 163a, 163b are provided in the form of a single two-stage heat pump compressor. Such two-stage heat pump compressors are known in the art. Further, the first and second overhead loops are preferably connected together in series as shown in FIG. 2, but these loops or circuits can be linked in parallel as well.

FIG. 3 illustrates an additional embodiment where the column 174a pressure (and therefore column temperatures) is not determined by the trim condenser 172 temperature. In the system 144a shown in FIG. 3, an additional suction drum 191 and third stage heat pump compressor 163c are placed upstream of the trim condenser 172a. The third stage heat pump compressor 163c compresses only enough vapor to satisfy the trim condenser 172a requirement or up to a pressure where that vapor will condense at the trim condenser 172a temperature, which is typically slightly above ambient. In this way, the operating temperature of the column 174a can be decoupled from the trim condenser 172a temperature. Again, the reboilers 164 and 168 may be stab-in-type heat exchangers disposed within the vessel 174a.

The disclosed processes and schemes may be practiced in the absence of any element, part, step, component, or ingredient which is not specifically disclosed herein.

What is claimed is:

1. A splitter system for separating a first material from a feed mixture of first and second materials, the system comprising:
   a column comprising a top, a bottom and a sidewall extending therebetween,
   a feed inlet connected to the sidewall for introducing a mixture of first and second materials into the column,
   an intermediate reboiler heat exchanger and a bottoms reboiler heat exchanger,
   the top comprising an overhead outlet connected to a first overhead loop and a second overhead loop, the first overhead loop connecting the overhead outlet to a first heat pump compressor, the second overhead loop connecting the overhead outlet to a second heat pump compressor, the first heat pump compressor for passing overhead material from the first overhead loop through the intermediate reboiler heat exchanger, the second heat pump compressor for passing overhead material from the second overhead loop through the bottoms reboiler heat exchanger.

2. The splitter of claim 1 wherein the first heat pump compressor and the second heat pump compressor are first and second stages of a two stage heat pump compressor.

3. The splitter of claim 1 wherein the first overhead loop passes through the first heat pump compressor and through a second receiving drum having a vapor outlet connected to second heat pump compressor and a liquid outlet connected to a first receiving drum, the first receiving drum having a vapor outlet connected to the first heat pump compressor and a liquid outlet connected to a reflux pump that is connected to a reflux inlet and a first product outlet.

4. The splitter of claim 3 wherein the second overhead loop is connected to the first overhead loop and the second overhead loop passes through the second heat pump compressor to a condenser before passing to the second receiving drum.

5. The splitter of claim 1 wherein the second overhead loop is connected to a third overhead loop, the third overhead loop connecting the second overhead loop to a condenser, the third overhead loop comprising a third heat pump compressor, the third heat pump compressor compressing material in the third overhead loop and passing said material to the condenser.

6. The splitter of claim 3 wherein the second overhead loop passes through the second heat pump compressor to a third overhead loop, the third overhead loop passing material from the second overhead loop through a third receiving drum, through a third heat pump compressor and through a condenser before passing the material to the first receiving drum.

7. The splitter of claim 4 wherein the second heat pump compressor passes pressurized overhead material from the second overhead loop, through the bottoms reboiler heat exchanger and into the second receiving drum.

8. The splitter of claim 1 further comprising
a bottoms outlet connected to a bottoms loop that passes through the bottoms reboiler before returning to the column, and
an intermediate loop connected to the column below the feed and passing through the intermediate heat exchanger before returning to the column below the feed.

9. The splitter of claim 3 wherein a molar ratio of material entering the column through the reflux inlet to material entering the column through the feed inlet (R/F) is at least 5.

10. The splitter of claim 1 wherein the feed inlet is positioned at a theoretical stage where a composition in the column at said stage closely approximates a composition of the feed mixture.

11. The splitter of claim 1 wherein the first overhead loop delivers more heat to the intermediate reboiler heat exchanger than the second overhead loop delivers to the bottoms reboiler heat exchanger.

12. A method for separating a first material from a mixture of the first material and a second material, the method comprising:
introducing the mixture into a column through a feed inlet disposed between a top and a bottom of the column,
exposing material from the column below the feed inlet to an intermediate reboiler heat exchanger,
exposing bottoms material from the column to a bottoms reboiler heat exchanger,
circulating overhead vapor taken from the top of the column through first and second overhead loops, the first overhead loop connecting the overhead outlet to a first heat pump compressor, the second overhead loop connecting the overhead outlet to a second heat pump compressor,
compressing overhead vapor in the first overhead loop and circulating said compressed overhead vapor through the intermediate reboiler heat exchanger to heat the intermediate material exposed to the intermediate reboiler,
compressing overhead vapor in the second overhead loop and circulating said compressed overhead vapor through the bottoms reboiler heat exchanger to heat the bottoms material exposed to the bottoms reboiler.

13. The method of claim 12 wherein the first heat pump compressor and the second heat pump compressor are first and second stages of a two stage heat pump compressor.

14. The method of claim 12 further comprising
circulating at least some material from the second overhead loop through a third overhead loop, wherein the third overhead loop connects the second overhead loop to a third heat pump compressor and a condenser, and
compressing overhead vapor in the third overhead loop and circulating said compressed overhead vapor through the condenser.

15. The method of claim 14 further comprising
passing condensed material from the third overhead loop to the first overhead loop.

16. The method of claim 12 wherein the first material is propylene and the second material is propane.

17. The method of claim 12 wherein the first overhead loop delivers more heat to the intermediate reboiler heat exchanger than the second overhead loop delivers to the bottoms reboiler heat exchanger.

18. The method of claim 15 further comprising withdrawing propylene from the first overhead loop and withdrawing propane from a bottoms loop that passes from a bottoms outlet and through the bottoms reboiler before returning to the column.

19. A method for separating propylene from a mixture of the propylene and propane, the method comprising:
introducing the mixture into a column through a feed inlet disposed between a top and a bottom of the column,
exposing material from the column and below the feed inlet to an intermediate reboiler heat exchanger,
exposing material from the bottom of the column to a bottoms reboiler heat exchanger,
circulating overhead vapor taken from the top of the column through first and second overhead loops, the first overhead loop connecting the overhead outlet to a first heat pump compressor, the second overhead loop connecting the first overhead loop to a second heat pump compressor,
compressing overhead vapor in the first overhead loop and circulating said compressed overhead vapor through an intermediate reboiler heat exchanger to heat and at least partially vaporize the material from the column exposed to the intermediate reboiler heat exchanger,
compressing overhead vapor in the second overhead loop and circulating said compressed overhead vapor through the bottoms reboiler heat exchanger to heat and at least partially vaporize the material from the column exposed to the bottoms reboiler heat exchanger,
withdrawing propylene from the first overhead loop, and withdrawing propane from the second overhead loop.

20. The method of claim 19 wherein the first heat pump compressor and the second heat pump compressor are first and second stages of a two stage heat pump compressor.

* * * * *